US010980938B2

(12) United States Patent
Barmaimon et al.

(10) Patent No.: US 10,980,938 B2
(45) Date of Patent: Apr. 20, 2021

(54) DOUBLE ACTION RIGID FLUID PATH CONNECTOR (71) Applicant: FLEX LTD., Singapore (SG)

(72) Inventors: Eyal Barmaimon, Haifa (IL); Lior Shtram, Tel-Aviv (IL); Shai Finkman, Haifa (IL); Itay Landsman, Pardes-Hanna (IL)

(73) Assignee: FLEX LTD., Singapore (SG)

( * ) Notice: Subject to any disclaimer, the term of this patent is extended or adjusted under 35 U.S.C. 154(b) by 51 days.

(21) Appl. No.: 16/168,316

(22) Filed: Oct. 23, 2018

(65) Prior Publication Data

US 2019/0275235 A1 Sep. 12, 2019

Related U.S. Application Data (60) Provisional application No. 62/640,433, filed on Mar. 8, 2018.

(51) Int. Cl.
A61M 5/142 (2006.01)
A61M 5/24 (2006.01)
A61M 5/158 (2006.01)

(52) U.S. Cl.
CPC ...... A61M 5/14248 (2013.01); A61M 5/2466 (2013.01); A61M 5/158 (2013.01);
(Continued)

(58) Field of Classification Search
CPC .. A61M 5/162; A61M 5/158; A61M 5/14248; A61M 5/2466;
(Continued)

(56) References Cited

U.S. PATENT DOCUMENTS 8,475,410 B2 * 7/2013 Kaufmann .......... A61M 5/3287
604/136
8,932,256 B2 * 1/2015 Chong .................. A61M 5/158
604/156
(Continued)

FOREIGN PATENT DOCUMENTS

WO 2012108958 A1 8/2012
WO 2017007952 A1 1/2017

OTHER PUBLICATIONS

International Search Report and Written Opinion dated Jun. 19, 2019 in corresponding International Patent Application No. PCT/IB2019/051911.

Primary Examiner — Nathan R Price
Assistant Examiner — Anna E Goldberg-Richmeier
(74) Attorney, Agent, or Firm — Volpe Koenig (57) ABSTRACT A device and method for creating a fluid path are disclosed. A patch pump may include a start button. A force may be applied on a button needle in a force direction, based on activating the start button. A first end of the button needle may puncture a fluid container by moving the button needle from a first button needle position to a second button needle position via the force in the force direction. A second end of the button needle may be positioned underneath a carrier septum contained in a carrier, via the applied force. The carrier may be released based on activating the start button and the second end of the button needle, based on releasing the carrier, may puncture the carrier septum. A fluid path may be provided form the fluid container to a patient's tissue based on puncturing the fluid container and the carrier septum.

11 Claims, 8 Drawing Sheets (52) U.S. Cl.
CPC ............ *A61M 2005/14252* (2013.01); *A61M 2005/1585* (2013.01); *A61M 2005/2474* (2013.01)

(58) Field of Classification Search
CPC ........... A61M 2005/14252; A61M 2005/2474; A61M 2005/1585
See application file for complete search history.

(56) References Cited

U.S. PATENT DOCUMENTS

| | | | |
|---|---|---|---|
| 2011/0178472 A1* | 7/2011 | Cabiri ................. | A61M 5/3287 604/198 |
| 2013/0197474 A1* | 8/2013 | Bilton ................. | A61M 5/2448 604/506 |
| 2016/0082182 A1* | 3/2016 | Gregory ............ | A61M 5/14526 604/150 |
| 2018/0193554 A1* | 7/2018 | Meehan ............ | A61M 5/14248 |

* cited by examiner

DOUBLE ACTION RIGID FLUID PATH CONNECTOR

This application claims the benefit of U.S. Provisional Application No. 62/640,433 having a filing date of Mar. 8, 2018, which is incorporated by reference as if fully set forth.

BACKGROUND

There is a strong market need for an apparatus that can enable the delivery or administration of solutions such as medication in a wearable format. For instance, the treatment of diabetes requires the subcutaneous delivery of insulin. As a result, wearable pumps that deliver a medication to a patient may be used to administer such solutions. These pumps may incorporate the medication, pumping mechanism, and infusion set into a patch that attaches to a patient's skin, thus eliminating the need for external systems.

Patients may wear patch pumps for a prolonged period of time and, accordingly, patient comfort and ease of use is a consideration in the design and manufacturing of such patch pumps.

SUMMARY

A device and method for creating a fluid path are disclosed. A patch pump may include a start button, which may be activated. A force may be applied on a button needle in a force direction, based on activating the start button. A first end of the button needle may puncture a fluid container by moving the button needle from a first button needle position to a second button needle position via the force such that the first end of the button needle punctures a barrier of the fluid container by moving in the force direction. A second end of the button needle may be positioned underneath a carrier septum contained in a carrier, via the applied force. The carrier may be released based on activating the start button and the second end of the button needle, based on releasing the carrier, may puncture the carrier septum. A fluid path may be provided form the fluid container to a patient's tissue based on puncturing the fluid container and the carrier septum.

BRIEF DESCRIPTION OF THE DRAWINGS

A more detailed understanding may be had from the following description, given by way of example in conjunction with the accompanying drawings wherein.

DETAILED DESCRIPTION

Examples of different pumps, button needles and related components will be described more fully hereinafter with reference to the accompanying drawings. These examples are not mutually exclusive, and features found in one example can be combined with features found in one or more other examples to achieve additional implementations. Accordingly, it will be understood that the examples shown in the accompanying drawings are provided for illustrative purposes only and they are not intended to limit the disclosure in any way. Like numbers refer to like elements throughout.

Below are described an apparatus and methods for delivering solutions such as pharmaceutical drugs and/or biologics to a patient. The apparatus and methods may allow for prescription or standard off-the-shelf drug cartridges to be utilized without compromising the sterility of the solution. This may enable a patient to self-administer a solution in a self-contained wearable patch pump form factor that is cost effective and comfortable to wear. The disclosure subject matter provided herein may allow the manufacturing and use of a patch pump that is small enough in size to be comfortable to wear.

Figure 1A:
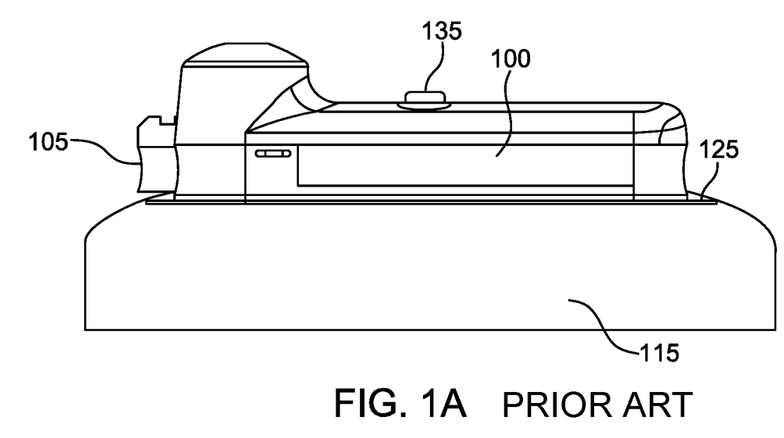
FIG. 1A is a graphic depiction of a patch pump on a user.

FIG. 1A is a graphic depiction of a patch pump 100 on a patient 115. The patch pump 100 includes a base 125 that contacts the patient's skin. In some embodiments, the base 125 includes an adhesive liner that affixes the patch pump 100 to the patient 115. The patch pump 100 may further include a user flow control switch 135. The user flow control switch 135 may enable a user to pause and control the flow rate of a solution. The patch pump 100 further includes a start button 105 that may be pressed by a user to cause a cannula and/or needle to be inserted into the patient and the solution to flow from a drug container 130 through the cannula and/or needle into the patient.

Figure 1B:
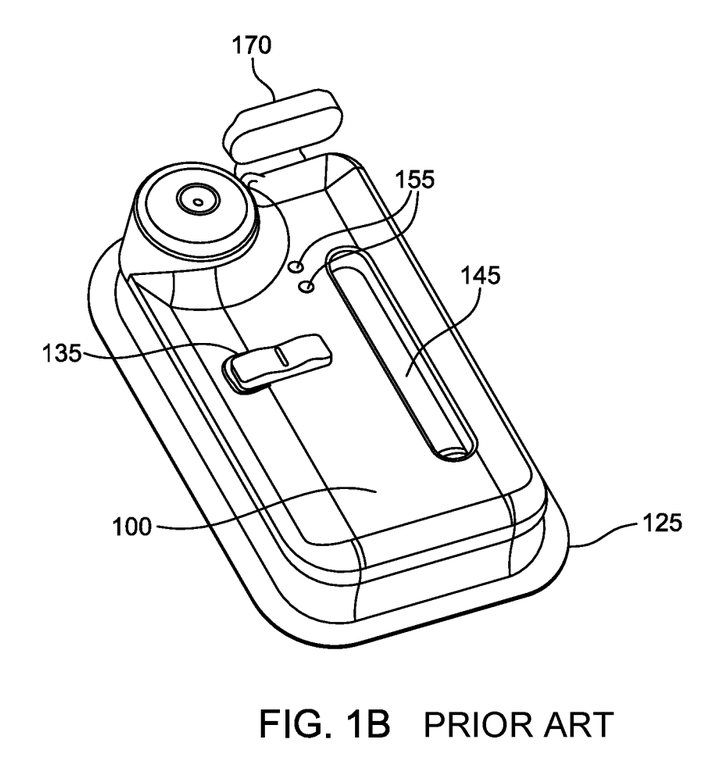
FIG. 1B is a graphic depiction of the outer casing of an embodiment of a patch pump.

As shown in FIG. 1B, the patch pump 100 may further include a drug viewing window 145. This viewing window may enable a user to view the amount of a solution that remains in the drug container 130. The patch pump 100 may also include one or more visual indicators 155. The visual indicators 155 provide feedback on the operational status of the system. The operational status of the system may include warnings such as an over/under temperature warning, drug expiration warning and over/under pressure warning. In addition, the operational status may include information indicating that the drug is being administered, how much time is remaining for the drug dosage to be completed and the current flow rate. The visual indicators may include LEDS, LCD displays or other similar display technologies known in the art. The information that is displayed by visual indicators may also be wirelessly transmitted to a mobile computing device such as a smart phone utilizing any of the wireless communication methods known in the art.

The patch pump 100 may further include a removable safety pin 170. The removable safety pin mechanically engages the start button 105 and prohibits the start button 105 from being involuntary pressed.

Figure 1C:
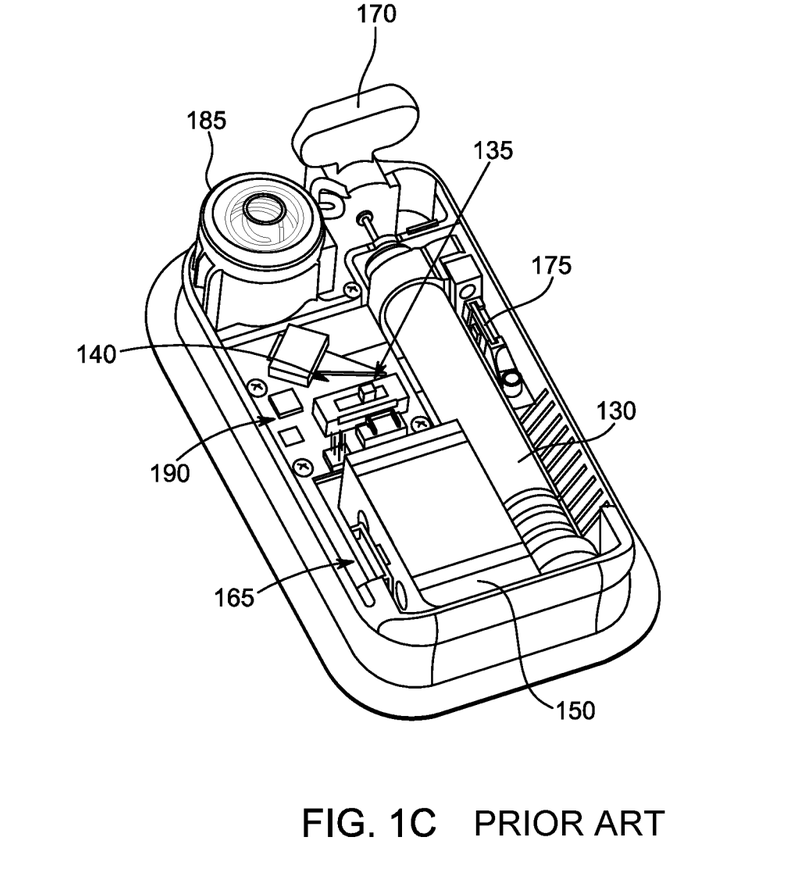
FIG. 1C is a graphic depiction of an embodiment of a patch pump with the outer casting removed.

FIG. 1C shows additional components of a patch pump 100. The patch pump 100 may also include a needle insertion component 185 that is mechanically connected to the start button 105. In addition, the patch pump 100 includes an electronic circuit board 140 that includes control circuitry for the visual indicators 155, user flow control switch 135 and a pressurization system 150. In addition, the electronic circuit board 140 may be communicatively connected to one or more sensors. These sensors may include pressure sensor 165 and proximity sensor 175. The electronic circuit board 140 may also include a memory 190. The memory 190 may store dosing instructions for the administration of the solution. In addition, the memory 190 may also store information regarding the administration of the solution. This information may include, time, date, and flow rate when the solution was administered. The electronic circuit board 140 may control the visual indicators 155 and the driving system 150 based on the information stored in the memory and the feedback from the sensors. The electronic circuit board 140 may include a communication module that enables the transmission of information stored in the memory 190 to a wireless computing device. In addition, the communication module may also receive updated dosing instructions that are subsequently stored in the memory 190.

A device, such as a patch pump, configured in accordance with the disclosed subject matter may consume a smaller footprint than traditional patch pumps. Such a device may include a button needle designed to create a fluid path from a drug container to a needle or cannula that can be inserted into a user's tissue. The button needle may be configured such that a movement of the button needle from a first position to a second position may cause the button needle to puncture a drug container via its first end and have its second end be positioned under a carrier's septum. The carrier may drop, causing the second end of the button needle to puncture the septum, effectively creating a fluid path from the drug container to a needle/cannula. It should be noted that the first end of the button needle may extend in a first plane and the second end of the button needle may extend in a second plane different than the first plane. As an example, a button needle may include a first end that extends from left to right in a horizontal plane and a second end that extends from bottom to top in a vertical plane. Creating a fluid path by puncturing in two different planes may allow a patch pump device to be smaller than a fluid path created by puncturing along the same plane.

Figure 2A:
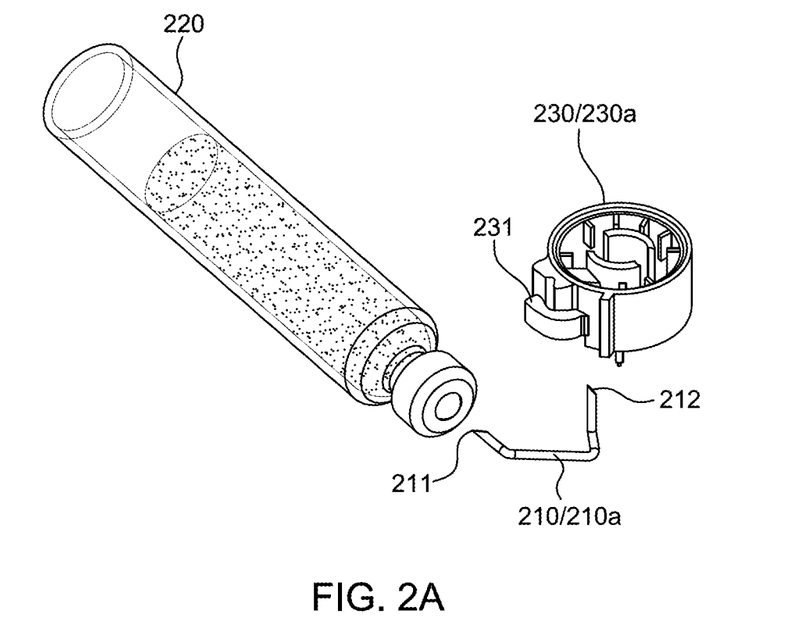
FIG. 2A is a graphical depiction of a button needle at a first position, a drug container, and a carrier arm at a first position.

FIG. 2A is a graphical depiction of a button needle 210 at a first position 210a. As shown, the button needle 210 includes a first end 211 that extends in a first direction and a second end 212 that extends in a second direction different than the first direction. It will be understood that FIG. 2A-C includes components, including a drug container 220 and a carrier 230 including a septum 231, which may be included in a patch pump such as the patch pump of FIGS. 1A-C or may be part of a different patch pump or other solution delivery mechanism which requires the use of a fluid path. Accordingly, the button needle 210 may be configured to operate with the components shown in FIGS. 1A-C or, alternatively, may be configured to operate with a subset of the components shown in FIGS. 1A-C or none of the components shown in FIGS. 1A-C. Patch pumps with different or modified components than those shown in FIGS. 1A-C may be used with a button needle 210, as disclosed herein.

As shown in FIG. 2A, a carrier 230 including a septum 231 may be in a first position 230a. The first position 230a may be a position such that the second end 212 of the button needle 210 does not align with the septum 231. Additionally, as shown, a drug container 220 may be aligned with the first end 211 of the button needle 210 such that the first end 211 of the button needle 210 faces a membrane of the drug container 220.

Figure 2B:
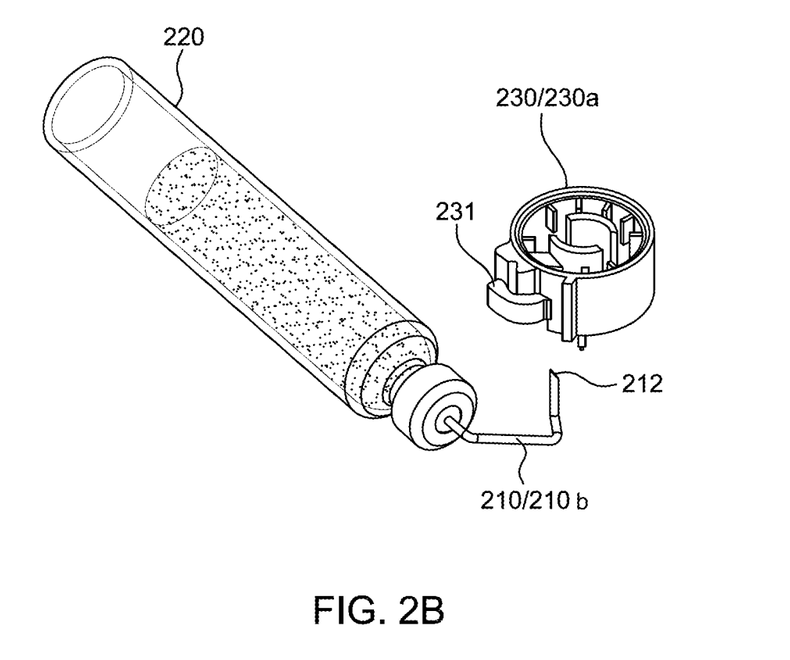
FIG. 2B is a graphical depiction of a button needle at a second position engaged with the drug container and a carrier arm at a first position.

The button needle 210 may move from the first position 210a from FIG. 2A to the second position 210b of FIG. 2B. As shown in FIG. 2B, the button needle 210 may move to the second position 210b such that the first end 211 (not shown in FIG. 2B) of the button needle 210 punctures a membrane of the drug container 220. The membrane of drug container 220 may be punctured by the first end 211 of the button needle 210 as a result of the first end 211 being sharp, as a result of the force applied to move the button needle 210 from its first position 210a to its second position 210b, or as a result of a combination of these or any other applicable factors.

Figure 2C:
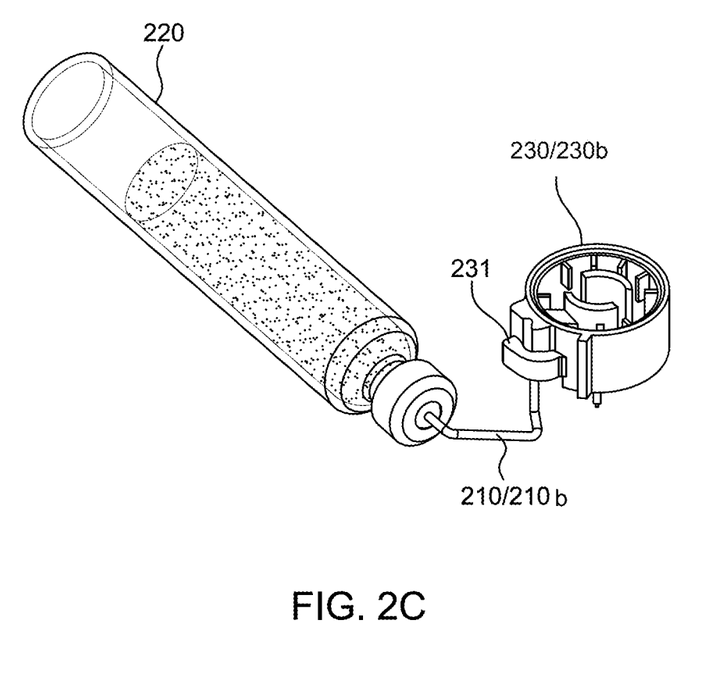
FIG. 2C is a graphical depiction of a first end and a second end of a button needle in a patch pump with a carrier arm both in their second position.

Additionally, as shown in FIG. 2B, the button needle 210 may move to the second position 210 b such that the second end 212 of the button needle 210 may align with the carrier septum 231 based on the movement of the button needle 210 to the second position 210 b. As shown in FIG. 2C, the carrier 230 may move from a first position 230 a to a second position 230 b such that the second end 212 (not shown in FIG. 2C) of the button needle 210 punctures the septum 231. The septum 231 may be punctured by the second end 212 of the button needle 210 as a result of the second end 212 being, sharp, as a result of the applied force which moves the carrier 230 from its first position 230 a to its second position 230 b, or as a result of a combination of these or any other applicable factors.

It should be noted that the button needle 210 may effectively create a fluid path from the drug container 220 to the carrier by moving from a first position 210a to a second position 210b and by its first end 211 puncturing a membrane of a drug container 220 and its second end 212 aligning to puncture a carrier septum 230 as the carrier septum 230 moves from its first position 230a to its second position 230b. As further disclosed herein, the fluid path may enable fluid from the drug container to reach a user via a needle and/or cannula.

Figure 3:
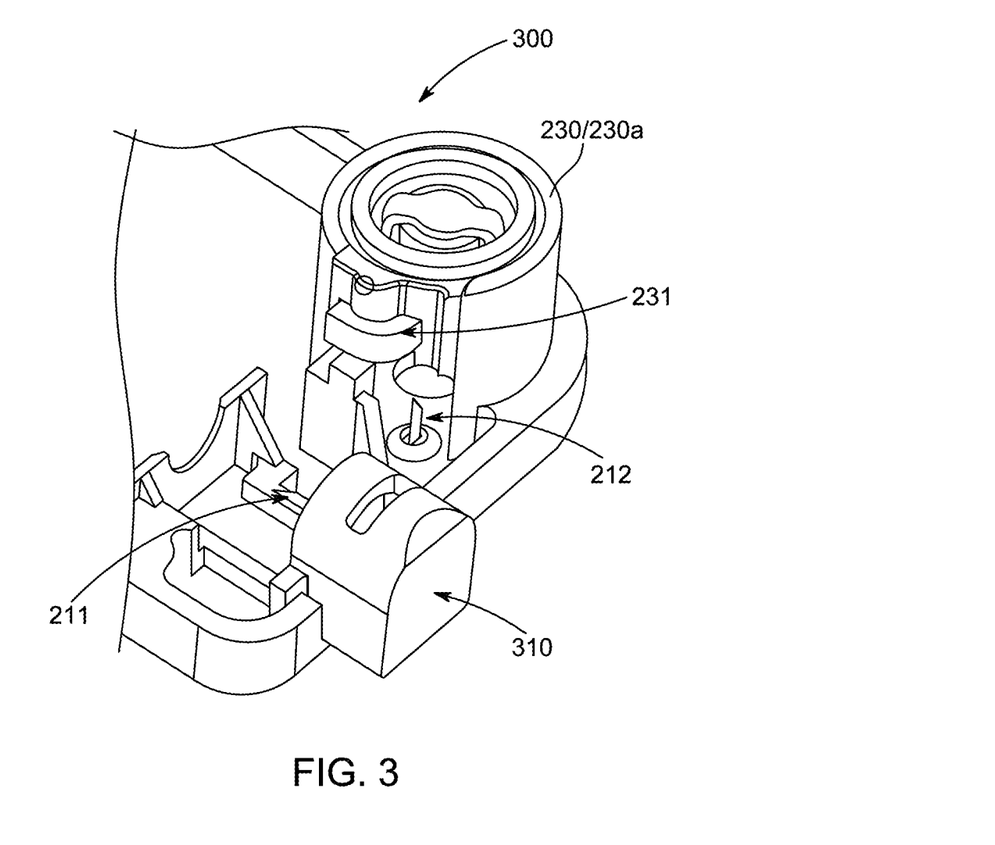
FIG. 3 is a graphical depiction of a patch pump with a needle hub and fluid path.

FIG. 3 shows a patch pump 300 that includes the carrier 230 at a first position 230a. The carrier 230 includes the carrier septum 231. A push button 310 may be pressed such that the first end 211 of a button needle moves in the direction that the push button 310 traverses, when pressed. The first end 211 of the button needle may puncture a membrane of a drug container (not shown). Additionally, the second end 212 of the button needle may also move in the direction that the push button 310 traverses, when pressed. The second end 212 of the button needle may move such that it aligns with the carrier septum 231 where, when the carrier 230 moves from a first position 230a to a second position 230b, as shown in FIG. 2C, the second end 212 punctures the carrier septum 231.

Figure 4A:
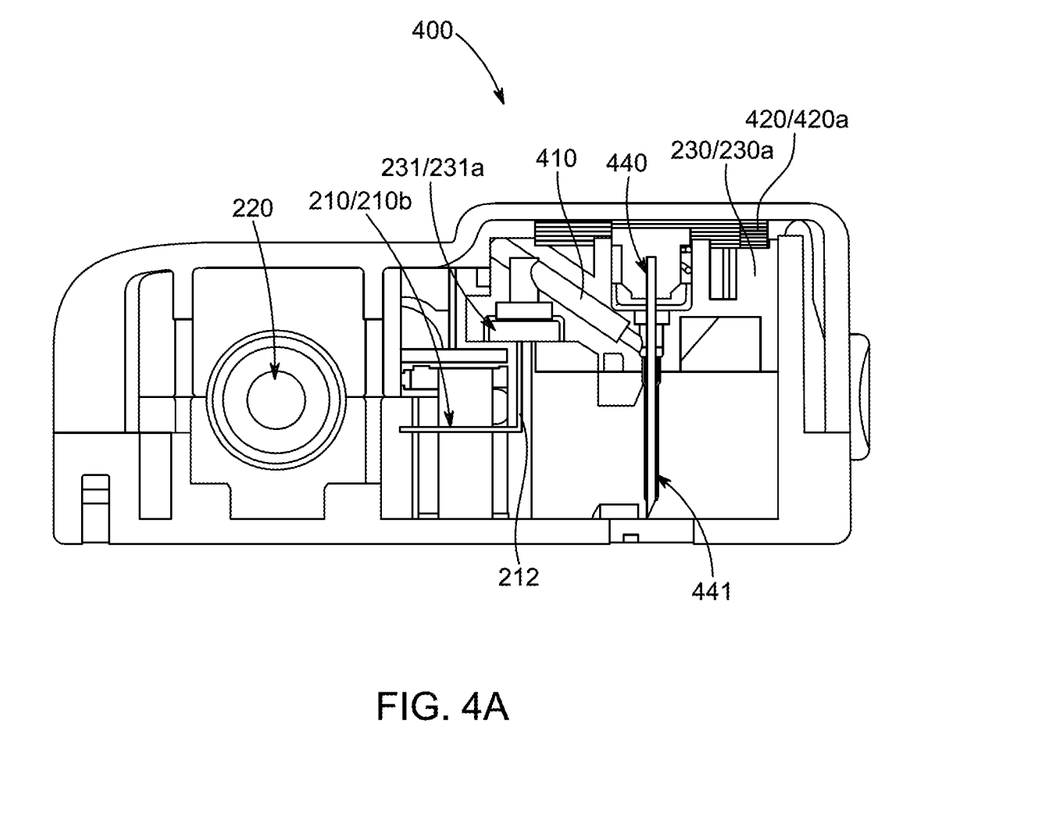
FIG. 4A is a graphical depiction of a patch pump with detailed needle hub and fluid path.

FIG. 4A shows a cross section of a patch pump 400 in accordance with the disclosed subject matter. It will be understood that FIG. 4A and FIG. 4B include components, including a drug container 220 and a carrier 230 including a carrier septum 231 at carrier septum position 231a, which may be included in a patch pump such as the patch pump of FIGS. 1A-C or may be part of a different patch pump or other solution delivery mechanism which requires the use of a fluid path. Accordingly, the button needle 210 configured to operate with the components shown in FIGS. 1A-C or, alternatively, may be configured to operate with a subset of the components shown in FIGS. 1A-C or none of the components shown in FIGS. 1A-C. Patch pumps with different or modified components then those shown in FIGS. 1A-C may be used with a button needle 210, as disclosed herein.

Figure 4B:
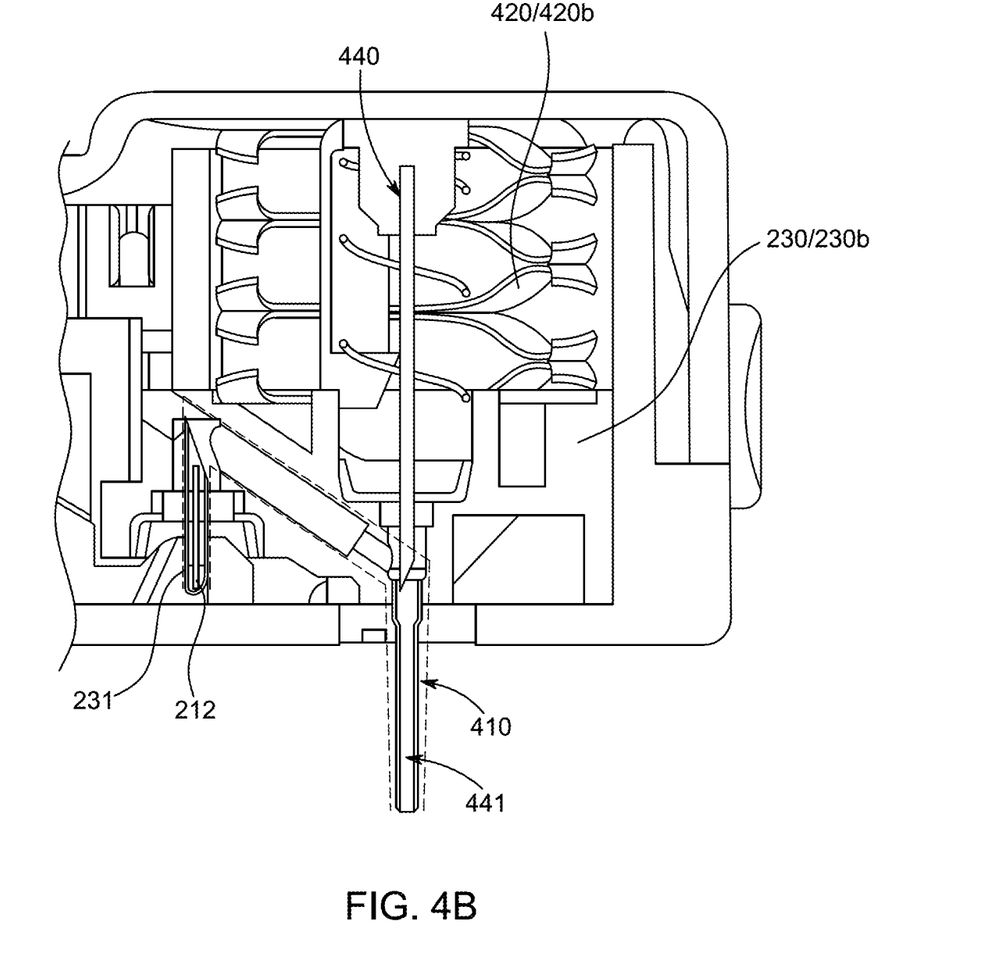
FIG. 4B is another graphical depiction of a patch pump with a needle hub insertion mechanism.

As shown in FIG. 4A, the button needle 210 may be at a second position 210*b* such that its second end 212 aligns with the carrier septum 231. The carrier 230 may be in its first position 230*a* and the carrier septum 231 may be aligned with the second end 212 such that when the carrier 230 moves to its second position, as shown in FIG. 4B, the second end 212 of the button needle 210 punctures the carrier septum 231. FIG. 4A also shows a primary spring 420 in a first primary spring state 420*a* such that the first primary spring state 420*a* is a compressed state. Additionally, a needle 440 and cannula 441 are also shown in FIG. 4A. The needle 440 may be configured to apply a force onto cannula 441 such that the cannula 441 is inserted into a user's tissue, as further disclosed herein.

FIG. 4B shows the patch pump 400 of FIG. 4A after the carrier 230 moves from its first position 230*a* from FIG. 4A to its second position 230*b* of FIG. 4B. As shown, the primary spring 420 may move from a first spring state 420*a* of FIG. 4A to the second spring state 420*b* of FIG. 4B. The second spring state 420*b* may be an expanded spring state such that the carrier 230 is moved to its second position 230*b* as a result of the carrier spring 420 expanding to its second spring state 420*b*. As a result of the carrier moving to its second position 230*b*, the needle 440 may cause the cannula to move down into a user's tissue. Additionally, the septum 231 may also move with the carrier 230 such that the second end 212 of the button needle 210 punctures the septum.

As shown in FIG. 4B, a fluid path 410 may be created as a result of the second end 212 of the button needle 210 puncturing the septum 231 and the cannula 441 moving down into a user's tissue. A first end of the fluid path 410 may be at the fluid container 220 of FIGS. 2A-C. The fluid path may continue via the first end 211 of button needle 210 of FIGS. 2A-C, traverse through the button needle 210 through the second end 212, as shown in FIG. 4B, and end at a user's tissue via cannula 441. It should be noted that the button needle 210, which includes components in at least two different planes, may enable the fluid path 441 to occupy a smaller footprint than if the button needle or like connector was a linear needle. A patch pump with a button needle that occupies two different planes, as disclosed herein, may allow for the button needle to connect a drug container to a user's tissue such that the patch pump occupies a smaller footprint than if the button needle was not used in the patch pump.

According to an implementation of the disclosed subject matter, the patch pump, such as the patch pump 100 of FIGS. 1A-C may provide one or more positive or negative indications based on puncturing the fluid container and/or the carrier septum. For example, visual indicators 155 or similar indicators may be used to provide an error indication when the fluid container is not sufficiently punctured, such as by the first end of a button needle (not shown in FIGS. 1A-C). Alternatively or in addition, visual indicators 155 or similar indicators may be used to provide an error indication when the carrier septum is not sufficiently punctured, such as by the second end of a button needle (not shown in FIGS. 1A-C). Alternatively or in addition, visual indicators 155 or similar indicators may be used to provide an positive indication when the fluid container and carrier septum is sufficiently punctured, such as by the first end and second end, respectively, of a button needle (not shown in FIGS. 1A-C).

Figure 5:
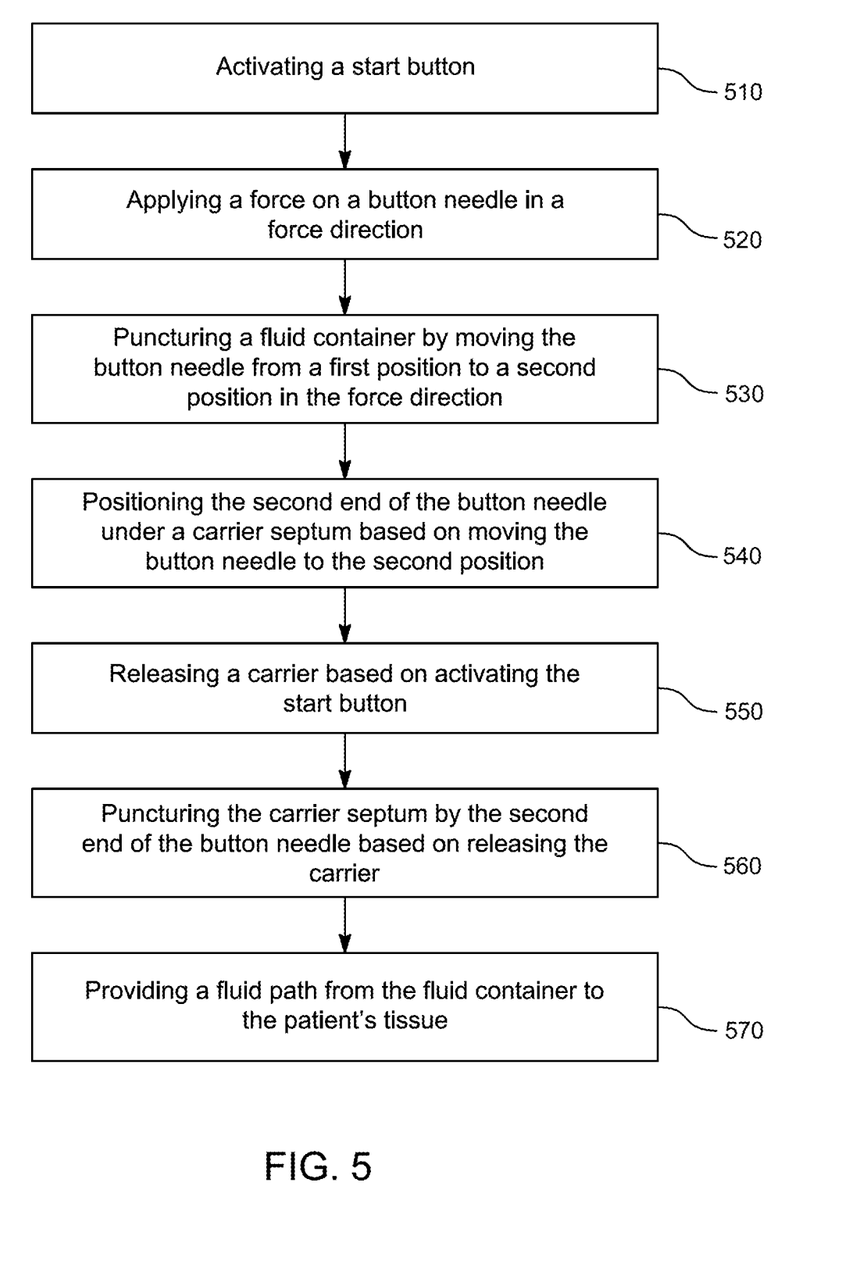
FIG. 5 is a flowchart for providing a fluid path via a button needle.

The patch pump 300 or 400 may be configured to provide a fluid path from a drug container via a button needle, as outlined in the flowchart provided in FIG. 5. As shown in FIG. 5, at 510 a start button, such as the start button 310 of FIG. 3, may be activated. The start button 310 may be activated as a result of a user pressing the start button 310. A threshold amount of force may be applied to modify the state of the start button 310 from an inactive state to an activated state such that a minor or accidental force applied to the start button 510 does not activate the start button. The start button 310 may move from a first position to a second position, upon being activated.

At 520 in FIG. 5, a force may be applied on a button needle, such as the button needle 210 with first end 211 and second end 212, as shown in FIGS. 3-4B. The force may be applied in a force direction where the force direction corresponds to the direction that the start button 310 moves from its first position to its second position. According to this implementation, the force applied to the button needle 210 may be the same force that moves the start button 310 from its first position to its second position. Alternatively, the force direction may correspond to the direction in which the first end 211 of the button needle 210 would need to traverse to puncture the drug container 220. The force applied on the button needle 210 may be applied based on a mechanical movement, an electronic movement, or the like.

At 530 in FIG. 5, a fluid container, such as the drug container 220 may be punctured by moving a button needle, such as the button needle 210, from a first position to a second position. As shown in FIG. 3, the first end 211 of the button needle may face the drug container 220 (shown in FIG. 4A). By moving from its first position in to its second position, the push button 220 may apply a force onto the button needle 210 such that the first end 211 of the button needle punctures a membrane of the drug container 220, as shown in FIG. 2B.

At 540 in FIG. 5, a second end of a button needle, such as the second end 212 of the button needle 210 of FIGS. 2A-4B, may be positioned under a carrier septum, such as the carrier septum 230, based on moving the button needle 210 to the second position. As shown in FIG. 2A, the second end 211 of the button needle is at a first position. By moving from its first position to its second position, the push button 310 may apply a force onto the button needle 210 such that the second end 212 of the button needle 210 moves from its first position of FIG. 2A to its second position of FIG. 2B, as the button needle moves from position 210*a* to 210*b*. As shown, based on the movement of the button needle, the second end 212 may be positioned under a carrier septum 231.

At 550 of FIG. 5, a carrier, such as the carrier 230 of FIGS. 2A-4B, may be released. The carrier 230 may be released as a result of the activation of the start button 310. The carrier may include the carrier septum 231 and, when released, may move from a first position 231*a*, as shown in FIG. 4A to a second position 231*b* as shown in FIG. 4B. It should be noted that the second end 212 of the button needle may pierce the carrier septum 231 when the carrier septum 231 moves from its first position 231*a* of FIG. 4A to its second position 231*b* of FIG. 4B. At 560 of FIG. 5, the carrier septum 231 may be punctured by the second end 212 of the button needle 210, based on releasing the carrier 230.

At 570 of FIG. 5, a fluid path, such as the fluid path 410 of FIG. 4B may be provided from the fluid container 220, as shown in FIG. 4A to a user's tissue via a cannula, such as cannula 441. Notably, as shown in FIGS. 4A-B the fluid path 410 may include the fluid container 220, first end 211 of the button needle 210, second end 212 of the button needle 210, carrier septum 231, one or more connecting components (not shown), and cannula 441. As an example, fluid from the fluid container 220 may flow via the first end 211 of the button needle 210, into the second end 212 of the button needle 210, through a carrier septum 231, a connecting component, and into a cannula 441. The fluid may enter a user's tissue via the cannula 441.

Although features and elements are described above in particular combinations, one of ordinary skill in the art will appreciate that each feature or element can be used alone or in any combination with the other features and elements.

What is claimed is:

1. A device comprising:
   a start button configured to activate a force to be applied to a button needle;
   the button needle comprising a first end and a second end and configured to move from a first button needle position to a second button needle position based on the force;
   the first end configured to puncture a fluid container when the button needle moves from the first button needle position to the second button needle position;
   a carrier comprising a carrier septum configured to move from a first carrier position to a second carrier position;
   the second end configured to puncture the carrier septum when the button needle moves from the first button needle position to the second button needle position and the carrier moves from the first carrier position to the second carrier position, wherein a fluid path is created from the fluid container to a cannula via the button needle; and,
   wherein the button needle occupies at least two planes wherein a first plane corresponds to a direction of the first end of the button needle and a second plane corresponds to a direction of the second end of the button needle, wherein the first plane is a horizontal plane and the second plane is a vertical plane oriented perpendicular to the horizontal plane.

2. The device of claim 1, wherein the force is applied based on movement of the start button.

3. The device of claim 1 further comprising an indicator configured to provide a positive indication when the fluid container and carrier septum is sufficiently punctured.

4. The device of claim 1 further comprising a patient needle configured to release after the activation of the start button.

5. The device of claim 4, wherein the patient needle is configured to retract after the cannula is inserted into a patient.

6. The device of claim 1 configured to provide a solution from the fluid container to the cannula, via the fluid path.

7. A method comprising:
   activating a start button;
   applying a force on a button needle in a force direction based on activating the start button;
   puncturing a fluid container by a first end of the button needle by moving the button needle from a first button needle position to a second button needle position via the force wherein the first end of the button needle punctures a barrier of the fluid container by moving in the force direction;
   positioning, via the applied force, a second end of the button needle underneath a carrier septum contained in a carrier;
   releasing the carrier based on activating the start button;
   puncturing the carrier septum by the second end of the button needle based on the releasing the carrier;
   providing a fluid path from the fluid container to a patient's tissue based on puncturing the fluid container and puncturing the carrier septum; and,
   wherein the button needle occupies at least two planes wherein a first plane corresponds to a direction of the first end of the button needle and a second plane corresponds to a direction of the second end of the button needle, wherein the first plane is a horizontal plane and the second plane is a vertical plane oriented perpendicular to the horizontal plane.

8. The method of claim 7, wherein activating the start button comprises applying a force generated by a physical movement to move the start button from a first position to a second position.

9. The method of claim 7 further comprising providing a solution from the fluid container to a cannula via the fluid path.

10. The method of claim 9 further comprising:
    releasing a patient needle which is predisposed in the cannula; and
    inserting the cannula into a user's tissue with the patient needle; and
    retracting the patient needle from the cannula.

11. The method of claim 7 further comprising providing a positive indication when the fluid container and carrier septum are sufficiently punctured.

* * * * *